(12) United States Patent
Snyder

(10) Patent No.: US 9,913,824 B2
(45) Date of Patent: Mar. 13, 2018

(54) METHODS FOR INTERNALLY CONTROLLING OR TREATING EQUINE BOT LARVAE

(75) Inventor: Daniel Earl Snyder, Indianapolis, IN (US)

(73) Assignee: ELANCO US INC., Greenfield, IN (US)

( * ) Notice: Subject to any disclaimer, the term of this patent is extended or adjusted under 35 U.S.C. 154(b) by 753 days.

(21) Appl. No.: 13/515,603

(22) PCT Filed: Jan. 20, 2011

(86) PCT No.: PCT/US2011/021837
§ 371 (c)(1),
(2), (4) Date: Jun. 13, 2012

(87) PCT Pub. No.: WO2011/091122
PCT Pub. Date: Jul. 28, 2011

(65) Prior Publication Data
US 2012/0252746 A1 Oct. 4, 2012

Related U.S. Application Data

(60) Provisional application No. 61/297,928, filed on Jan. 25, 2010.

(51) Int. Cl.
*A61K 31/7048* (2006.01)
*A61K 31/343* (2006.01)

(52) U.S. Cl.
CPC ........ *A61K 31/343* (2013.01); *A61K 31/7048* (2013.01)

(58) Field of Classification Search
USPC ....................................................... 514/28
See application file for complete search history.

(56) References Cited

U.S. PATENT DOCUMENTS

| 6,001,981 | A * | 12/1999 | DeAmicis et al. | 536/7.1 |
| 6,664,237 | B1 * | 12/2003 | Snyder | 514/28 |
| 7,608,604 | B2 | 10/2009 | Comlay et al. | |
| 2005/0032716 | A1 * | 2/2005 | Lowe | A01N 43/90 514/28 |
| 2008/0108800 | A1 * | 5/2008 | Podhorez | C07H 17/08 536/7.1 |

FOREIGN PATENT DOCUMENTS

| CA | 2736209 A1 | 3/2011 |
| EP | 0 375 316 A1 | 6/1990 |
| WO | WO 01/11963 A1 | 2/2001 |
| WO | WO 02/077005 A1 | 10/2002 |
| WO | 2005112950 | 12/2005 |
| WO | 2006109069 | 10/2006 |
| WO | WO 2010/030501 A2 | 3/2010 |
| WO | WO 2010/126584 A1 | 11/2010 |

OTHER PUBLICATIONS

Klei, T. et al "Re-evaluation of ivermectin efficacy . . . " Vet. Parasitol. (2001) vol. 98, pp. 315-320.*
Dripps et al., "Spinetoram: How artificial intelligence combined natural fermentation with synthetic chemistry to produce a new spinosyn insecticide," Plant Health Progress, http://www.plantmanagementnetwork.org/pub/php/perspective/2008/spinetoram/, Aug. 22, 2008, Plant Management Network.
Otranto et al., "Species composition of *Gasterophilus* spp. (*Diptera, Oestridae*) causing equine gastric myiasis in southern Italy: Parasite biodiversity and risks for extinction," Veterinary Parasitology, 2005; 133:111-118, www.elsevier.com/locate/vetpar.
Otranto et al., "Species composition of *Gasterophilus* spp. (*Diptera, Oestridae*) causing equine gastric myiasis in southern Italy: Parasite biodiversity and risks for extinction," Veterinary Parasitology 133 (2005) 111-118.
Parasitol. Res., 2009, vol. 104, pp. 209-216.

* cited by examiner

*Primary Examiner* — Leigh C Maier
(74) *Attorney, Agent, or Firm* — McAndrews, Held & Malloy, Ltd.

(57) ABSTRACT

Provided are novel methods and formulations for orally controlling bot larvae in the gastrointestinal tract of equine animal using a spinosyn.

7 Claims, No Drawings

METHODS FOR INTERNALLY CONTROLLING OR TREATING EQUINE BOT LARVAE

This application claims priority to, and is a §371 of International Application No. PCT/US2011/021837, filed Jan. 20, 2011, which claims priority to U.S. Provisional Application No. 60/297,928, filed Jan. 25, 2010, each application of which is incorporated herein by reference in its entirety.

There are nine different species of *Gasterophilus* globally, with three species which commonly affect equine animals in North America: *Gasterophilus intestinalis*, *Gasterophilus nasalis*, and *Gasterophilus haemorrhoidalis*. These three are often referred to as horse bots, and the larvae of all three infest the gastrointestinal tract of the animal. The duration of such infestation is normally from two to twelve months, which represents a substantial portion of this pest's life cycle. At the end of this period, the larvae are expelled in the animal's feces.

Bots can cause from minor to serious problems to the host animal. Such include damage to the lining of the stomach or small intestine, irritation of the gastrointestinal membranes, stomach ulcers, gingivitis, colic, anemia, interference with the passage and digestion of food which may lead to stomach rupture, esophageal paralysis, peritonitis, and squamal cell tumors.

Efforts for controlling or treating bots have focused on breaking its life cycle. External treatments, include grooming, hair clipping, and sponging with warm water, provide limited benefit as these have to be repeated frequently and effectiveness is variable even if carried out under the best circumstances. Given that most of the life cycle of the pest occurs within the animal, internal treatments have at least a longer window in which to attempt to treat the animal. Avermectins, such as ivermectin, abamectin, and moxidectin, have proved effective for the internal treatment of bots.

While the use of these and other internal agents have been beneficial, alternative or improved formulations and methods are needed. Desirable formulations and methods would not only provide alternative therapies, but would also overcome at least some limitations of current therapies. Such limitations include toxicity and safety, efficacy (potency and duration), and resistance issues. As an example, current treatment options include the use of broad spectrum products which contain an avermectin and kill intestinal nematodes as well as bots. However, due to nematode resistance, other nematocides, such as benzimidizoles, are used, but which have no boticidal activity so the horse owner needs another agent to control or treat bots. Also impacting the beneficial use of internal therapies are administration obstacles, which include mode and recurrence of administration. For example, reducing the frequency of administration while maintaining efficacy is desirable, as dosing animals is often inconvenient and/or difficult.

The present invention encompasses methods and formulations for use in equine animals which provide alternative options for combating bots. Further, they overcome at least some of the identified limitations in the use of current agents. The invention provides methods of controlling or treating bot larvae in the gastrointestinal tract of an equine animal which comprises orally administering an effective amount of a spinosyn to the animal, as well as pharmaceutical formulations for orally controlling or treating bot larvae in the gastrointestinal tract of an equine animal which comprises an effective amount of a spinosyn and a physiologically acceptable carrier.

Spinosyns are naturally derived fermentation products. They are macrolides produced by cultivation of *Saccharopolyspora spinosa*. The fermentation produces many factors, including spinosyn A and spinosyn D (also called A83543A and A8354D). Spinosyn A and spinosyn D are the two spinosyns that are most active as insecticides. A product comprised mainly of these two spinosyns (65-95% spinosyn A and 5-35% of spinosyn B) is available commercially under the trade name "spinosad". The major spinosyn factor, spinosyn A, is known to have an excellent human and animal safety and toxicological profile.

Each spinosyn has a 12-membered macrocyclic ring that is part of an unusual tetracyclic ring system to which two different sugars are attached, the amino-sugar forosamine and the neutral sugar 2N,3N,4N-(tri-O-methyl)rhamnose. This unique structure sets the spinosyns apart from other macrocyclic compounds.

Spinosyn A was the first spinosyn isolated and identified from the fermentation broth of *S. spinosa*. Subsequent examination of the fermentation broth revealed that *S. spinosa* produced a number of spinosyns that have been called spinosyns A to J (A83543A to J). The primary components are spinosyns A and D. Additional spinosyns, lettered from K to W, have been identified from mutant strains of *S. spinosa*. The various spinosyns are characterized by differences in the substitution patterns on the amino group of the forosamine sugar, at selected sites on the tetracyclic ring system and on the 2N,3N,4N-(tri-O-methyl) rhamnose group.

Boeck et al. described spinosyns A-H and J (which they called A83543 factors A, B, C, D, E, F, G, H and J), and salts thereof, in U.S. Pat. No. 5,362,634 (issued Nov. 8, 1994); U.S. Pat. No. 5,496,932 (issued Mar. 5, 1996); and U.S. Pat. No. 5,571,901 (issued Nov. 5, 1996). Mynderse et al. described spinosyns L-N (which they called A83543 factors L, M and N), their N-demethyl derivatives, and salts thereof, in U.S. Pat. No. 5,202,242 (issued Apr. 13, 1993); and Turner et al. described spinosyns Q-T (which they called A83543 factors Q, R, S and T), their N-demethyl derivatives, and salts thereof, in U.S. Pat. No. 5,591,606 (issued Jan. 7, 1997) and U.S. Pat. No. 5,631,155 (issued May 29, 1997). Spinosyns K, O, P, U, V, W and Y are described, for example, by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation", pages 146-154 (1997).

Spinetoram is the common name for a mixture of 25-90%, preferably 50-90% (2R,3aR,5aR,5bS,9S,13S,14R,16aS, 16bR)-2-(6-deoxy-3-O-ethyl-2,4-di-O-methy-1-.alpha.-L-mannopyranosyloxy)-13-[(2R,5S,6R)-5-(dimethylamino) tetrahydro-6-methylpyran-2-yloxy]-9-ethyl-2,3,3a,4,5,5a, 5b,6,9,10,11,12,13,14,16a,16b-hexadecahydro-14-methyl-1H-as-indaceno[3,2-d]oxacyclododecine-7,15-dione (referred to as "dihydro-Et-J"), and 10-75%, preferably 10-50% (2R,3aR,5aS,5bS,9S,13S,14R,16aS,16bS)-2-(6-deoxy-3-O-ethyl-2,4-di-O-methy-1-.alpha.-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13, 14,16a,16b-tet-radecahydro-4,14-dimethyl-1H-as-indaceno [3,2-o]oxacyclododecine-7,15-dione (referred to as "Et-L"). (Podhorez et al., US 2008/0108800A1). Spinetoram is described as providing long-lasting control of a broad spectrum of insect pests in a variety of crops (Dow AgroSciences Spinetoram Technical Bulletin, November 2006). It has been reported spinetoram has been registered in New Zealand as an insecticide in the pome fruit market ("Dow AgroSciences Receives First Global Registration for Spinetoram Insecticide," Dow AgroSciences Newsroom, Corporate News, Aug. 10, 2007).

The term "spinosyn" or "spinosyn component" as used herein refers to an individual spinosyn factor (spinosyn A, B, C, D, E, F, G, H, J, K, L, M, N, O, P, Q, R, S, T, U, V, W or Y), an N-demethyl derivative of an individual spinosyn factor, a physiologically acceptable salt thereof, or a combination thereof. The terms also include spinetoram or a physiologically acceptable salt thereof.

The spinosyns can react to form salts that are also useful in the methods and formulations of this invention. The salts are prepared using standard procedures for salt preparation. For example, spinosyn A can be neutralized with an appropriate acid to form an acid addition salt. The acid addition salts of spinosyns are particularly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

An equine animal is a member of the family Equidae and includes horses, donkeys, and mules.

"Controlling or treating" refers to either ameliorating or eliminating a current infestation, or preventing an infestation, in an equine animal host.

"Effective amount" refers to the amount of a spinosyn sufficient to control or treat bot larvae in the gastrointestinal tract of an animal, and includes causing a measurable reduction in the larvae population, and/or a reduction in the number or severity of related symptoms. Further, such amount should result in no or few adverse events in the treated equine animal. As those familiar with the art will understand, this amount will vary depending upon a number of factors. These factors include, for example, the type of equine animal being treated, its weight and general physical condition, and the dosing regimen. Ranges for spinosyns range from about 1 to about 100, desirably 5 to 50, and more desirably from about 10 to about 20, mg/kg of weight of the equine animal.

"Physiologically acceptable" as used in this application, for example with reference to salts and formulation components such as carriers and ingredients, means relatively non-toxic and safe when administered to the equine animal.

The formulations and methods of this invention may further include, in combination with the spinosyn component, one or more other active ingredients that have activity against bots or other pests. Examples of such include synthetic pyrethroids, natural pyrethins, organophosphates, organochlorines, carbamates, foramidines, avermectins, milbemycins, insect growth regulators (including chitin synthesis inhibitors, juvenile hormone analogs, and juvenile hormones), nitromethylenes, pyridines and pyrazoles.

"Oral formulation" means that the spinosyn component or components, either alone or in combination with one or more of the other types of compounds listed supra, is formulated into a product or formulation suitable for administering to the equine animal by mouth. These products or formulations include, but are not limited to, tablets, capsules, liquids, gels, pastes, oral sprays, buccal formulations, powders and animal feeds containing the active component or components. Generally, such formulations include a physiologically acceptable carrier. Such carriers are well known in the veterinary arts. The amount of the spinosyn in such an oral formulation may be from greater than 0% to 95%, desirably 0.1% to 60%, and more desirably 1% to 50%, all weight percentages. An example of a suitable oral formulation is Elector PSP, which contains approximately 44.2% w/w, or 452.8 g/L, of spinosad.

"Carrier" is used herein to describe any ingredient other than the active components in a formulation. The choice of carrier will to a large extent depend on factors such as the particular formulation, the effect of the carrier on solubility and stability, and the nature of the dosage form. Examples of carriers are well known in the art, and include excipients, diluents, stabilizers, and adjuvants.

The phrase "single-dose oral formulation" means that one oral dose of the formulation effectively controls or treats the bot larvae infestation for a prolonged time. The phrase "prolonged time" or "long-acting" comprises a period of at least 7 days, preferably a period of at least two weeks, and more preferably at least 30 days. The phrase "pulse dose oral formulation" means an oral formulation adapted for administration of a target total amount of a spinosyn in divided, distinct doses, normally administered over a short period of time such as a one or two day period. Pulse dosing is contrasted to single dosing in that while the therapeutic benefits are equal or substantially equivalent, the total dosing is carried out in more than one dosing over a short period of time. For instance, a total target dose may be pulse dosed by administering two, three, or four or more distinct, normally equal doses totaling the target dose over a one or two day period. Alternatively, a pulse dose may be accomplished by a single administration of the total target dose that is then released over time. This approach to pulse dosing can occur by having certain portions of the total dose released internally over time based on kinetics (e.g., every 2, 3, 4 or more hours) or based on location in the gastrointestinal tract (e.g., 50% in stomach, then 50% in the small intestine). For ease of administration, a single oral dosing is preferred.

This invention relates to an oral formulation, and its use, for controlling or treating bot larvae in the gastrointestinal tract of an equine animal, said formulation comprising an effective amount of a spinosyn, and a physiologically acceptable carrier, in an oral dosage form. The formulation may be a single-dose oral formulation or a pulse-dose oral formulation. Desirably, when a single-dose formulation, it will be administered not more than once every seven days, more desirably not more than once every two weeks, and most desirably not more than once every thirty days. Also encompassed by the invention is the use of a spinosyn for the manufacture of a oral formulation for controlling or treating bot larvae in the gastrointestinal tract of an equine animal.

A study was carried out in which spinosad was administered to horses naturally infested with gastric dwelling bot larvae. In this case, *Gasterophilus intestinalis* was the primary bot, and was present in the animals with counts of equal to or greater than 25 larvae, as identified via gastroscopy. Eight horses were used in the study, divided into three treatment groups, with two in the first treatment group, and three each in the remaining two.

All the horses were dosed on Day 0, with the first treatment group being untreated (negative control) and receiving 20 ml of water orally. The second and third treatment groups received 10 mg/kg and 20 mg/kg oral doses of spinosad, respectively, using Elector PSP, delivered via stomach tube. Following dosing on Day 0, gastroscopies and bot counts were performed on all horses on Days 7. While a second bot count was planned for Day 14, this was not carried out due to the efficacy observed at Day 7. The animals were observed for adverse events. Efficacy against natural bot infestations were determined by comparing pre-dosing bot counts to post-dosing counts for each of the spinosad treated animals. Blood samples were obtained from the horses on Day 0 at 4 and 8 hours post dosing, and additional blood samples were obtained on day 1, 2, 5, 7, and 14 post dosing, to determine spinosad concentrations.

No adverse events were observed, and the calculated percent efficiency was 90% reduction in bot numbers of the second and third treatment groups, as compared to the first treatment group.

I claim:

1. A method of treating bot larvae in the gastrointestinal tract of an equine animal which consists essentially of orally administering as a single dose an effective amount of a spinosyn to said animal, wherein the effective amount is from about 10 mg/kg to about 20 mg/kg of equine animal body weight, and wherein said spinosyn is spinosad or a physiologically acceptable salt thereof or spinetoram or a physiologically acceptable salt thereof.

2. The method of claim 1 wherein said equine animal is a horse.

3. The method of claim 1 wherein said spinosyn is administered with a physiologically acceptable carrier.

4. The method of claim 1 wherein said bot larvae is *Gasterophilus intestinalis, Gasterophilus nasalis*, or *Gasterophilus haemorrhoidalis*.

5. The method of claim 1 wherein said administration is in the form of a tablet, capsule, liquid, gel, paste, oral spray, buccal formulation, powder or animal feed.

6. The method of claim 1 wherein said spinosyn is spinetoram or a physiologically acceptable salt thereof.

7. The method of claim 1 wherein said spinosyn is spinosad or a physiologically acceptable salt thereof.

* * * * *